(12) United States Patent
Ertel

(10) Patent No.: US 12,729,360 B2
(45) Date of Patent: Sep. 8, 2026

(54) BIOREACTOR, END PLATE FOR A BIOREACTOR AND DATA COMMUNICATION UNIT FOR AN END PLATE

(71) Applicant: EPPENDORF SE, Hamburg (DE)

(72) Inventor: Guido Ertel, Dormagen (DE)

(73) Assignee: EPPENDORF SE, Hamburg (DE)

( * ) Notice: Subject to any disclaimer, the term of this patent is extended or adjusted under 35 U.S.C. 154(b) by 1086 days.

(21) Appl. No.: 17/786,264

(22) PCT Filed: Dec. 10, 2020

(86) PCT No.: PCT/EP2020/085627
§ 371 (c)(1),
(2) Date: Jun. 16, 2022

(87) PCT Pub. No.: WO2021/122334
PCT Pub. Date: Jun. 24, 2021

(65) Prior Publication Data

US 2023/0024281 A1 Jan. 26, 2023

(30) Foreign Application Priority Data

Dec. 18, 2019 (EP) .................................... 19217334

(51) Int. Cl.
*C12M 1/06* (2006.01)
*C12M 1/00* (2006.01)
(Continued)

(52) U.S. Cl.
CPC ............ *C12M 27/02* (2013.01); *C12M 23/08* (2013.01); *C12M 23/28* (2013.01); *C12M 41/12* (2013.01);
(Continued)

(58) Field of Classification Search
None
See application file for complete search history.

(56) References Cited

U.S. PATENT DOCUMENTS 6,202,713 B1 3/2001 Drescher et al.
8,522,996 B2 9/2013 Beese et al.
(Continued)

FOREIGN PATENT DOCUMENTS

DE 102010029953 12/2011
DE 102016103456 8/2017
(Continued)

OTHER PUBLICATIONS

Japanese Search Report, Dec. 24, 2024.

*Primary Examiner* — William H. Beisner
(74) *Attorney, Agent, or Firm* — Dinsmore & Shohl LLP

(57) ABSTRACT

A bioreactor has a container, an end plate, an agitator, a drive unit, and at least one field device arranged in the interior, field device electronics, a data transmission unit arranged on the end plate, and a motor head piece coupled in terms of energy to the drive unit. At least one communication unit is coupled in terms of signaling to the motor head piece and includes an adapter piece, having adapter electronics which are electrically connected to the field device electronics of the field device, and a communicator piece. The adapter piece and the communicator piece are separate components which can be coupled to one another, wherein the motor head piece is a separate component which can be coupled to the communication units.

20 Claims, 4 Drawing Sheets

(51) Int. Cl.

| | |
|---|---|
| ***C12M 1/24*** | (2006.01) |
| ***C12M 1/34*** | (2006.01) |
| ***C12M 1/36*** | (2006.01) |
| ***G05B 19/042*** | (2006.01) |

(52) U.S. Cl.
CPC ............ *C12M 41/42* (2013.01); *C12M 41/48* (2013.01); *G05B 19/042* (2013.01)

(56) References Cited

U.S. PATENT DOCUMENTS

| | | | |
|---|---|---|---|
| 11,012,116 | B2 | 5/2021 | Schauble et al. |
| 2004/0029170 | A1 | 2/2004 | Wolfram et al. |
| 2015/0132840 | A1 | 5/2015 | Arnold et al. |
| 2016/0333303 | A1 | 11/2016 | West |
| 2020/0186196 | A1 | 6/2020 | Schäuble et al. |

FOREIGN PATENT DOCUMENTS

| | | | | |
|---|---|---|---|---|
| DE | 102017114851 | | 1/2019 | |
| EP | 1653306 | | 5/2006 | |
| EP | 1776998 | B1 * | 7/2008 | .......... B01F 27/0541 |
| EP | 2674479 | | 12/2013 | |
| EP | 2853584 | | 4/2015 | |
| EP | 3514223 | | 4/2019 | |
| JP | 2012044943 | | 3/2012 | |
| JP | 2015525073 | | 9/2015 | |
| WO | 9902961 | | 1/1999 | |
| WO | 2013053778 | | 4/2013 | |
| WO | 2013053779 | | 4/2013 | |
| WO | 2013150064 | | 10/2013 | |
| WO | 2013186294 | | 12/2013 | |
| WO | 2017129800 | | 8/2017 | |
| WO | 2021008788 | | 1/2021 | |
| WO | 2021008814 | | 1/2021 | |

* cited by examiner

BIOREACTOR, END PLATE FOR A BIOREACTOR AND DATA COMMUNICATION UNIT FOR AN END PLATE

CROSS-REFERENCE TO FOREIGN PRIORITY APPLICATION

The present application claims the benefit under 35 U.S.C. § 119(b), 119(e), 120, 121, 365(c), and/or 386(c) of PCT/EP2020/085627 filed Dec. 10, 2020, which claims priority to European Patent Application No. 19217334.2 filed Dec. 18, 2019.

FIELD OF THE INVENTION

The invention relates to a bioreactor, in particular, for culturing microorganisms and/or cell cultures, to an end plate for closing such a bioreactor, and to a data transmission unit for this end plate. The invention also relates to a method for providing a data transmission unit.

BACKGROUND OF THE INVENTION

Bioreactors, often also referred to as fermenters, are containers in which certain microorganisms, cells or plants are cultured, preferably under the most optimum, controlled, and reproducible conditions, in order to obtain cells themselves or parts of the latter or one of their metabolic products. For this purpose, bioreactors enclose a reaction chamber in which a culture medium can be accommodated.

A bioreactor may have a volume of a few milliliters on a laboratory scale, in particular, in screening, up to several thousand cubic meters on a production scale. On a laboratory scale, in particular, for the purposes of research and development, bioreactors having a volume of up to ten liters are preferably used. The bioreactors on a laboratory scale differ from a bioreactor on a production scale in terms of a power input and mass and material transport as well as the materials used. Bioreactors on a laboratory scale are often formed from glass and/or metal, in particular, stainless steel, since the bioreactors must be sterilized between different applications, preferably by means of hot steam sterilization in an autoclave. As an alternative to reusable bioreactors, it is also possible to use single-use bioreactors. Single-use bioreactors are used to carry out a single biological or biotechnological process and are then disposed of. As a result of a new single-use bioreactor, which is preferably sterilized in the production process, being provided for each individual process, the risk of contamination can be reduced and the effort needed to carry out a cleaning and sterilization process is dispensed with at the same time.

Bioreactors usually have an agitator, the agitator shaft of which can be caused to rotate by a drive unit. As a result, an agitator element connected to the agitator shaft in a torsionally rigid manner may likewise be caused to rotate and the substances present in the reaction chamber, in particular, the culture medium, can be thoroughly mixed. In particular, two or more agitator elements may also be arranged on the agitator shaft, preferably with an axial spacing, and may be connected to said agitator shaft. The agitator element(s) may also be formed in one piece with the agitator shaft.

In addition, bioreactors often have a plurality of connections, primary and secondary materials, and various instruments, for example, sensors and/or actuators, which can be introduced into the reaction chamber. Fluid lines, in particular, gas lines, such as gas introduction lines or exhaust gas lines, can preferably also be connected via these connections.

An optimum product yield can be strived for with the aid of the sensors and/or the actuators. For this purpose, use is generally made of sensors which monitor the conditions in the reaction chamber, in particular a pH value, a redox potential, an $O_2$ content in the culture medium and possibly the exhaust air, a $CO_2$ content in the exhaust air, a temperature, an optical density of the culture medium, foaming, a glucose content, a glycerin content, and/or a lactate content. Furthermore, various actuators, for example, Peltier coolers and/or light rods, may be provided in order to provide the most optimum culture conditions.

The sensors and actuators—if present—are connected to a corresponding measurement module and/or an evaluation unit and/or a control unit via a respective cable. These cables are generally well shielded and specifically constructed to safeguard the integrity of the data which may be considerably disrupted by external influences, for example, electromagnetic fields. The number of cables in the case of a plurality of sensors and/or actuators may result in a high degree of confusion. Furthermore, the number of cables restricts the handling of the bioreactor. The restriction in the handling is particularly noticeable, in particular, in the case of bioreactors having a smaller scale, for example in the region of 300 ml.

SUMMARY OF THE INVENTION

The invention is therefore based on the object of providing an improved solution which addresses at least one of the problems mentioned. In particular, an object of the invention is to provide a solution which is improved with respect to the handling of the bioreactor and simultaneously enables robust data transmission.

According to a first aspect, the object mentioned at the outset is achieved by means of a bioreactor, in particular, for culturing microorganisms and/or cell cultures, having a container, an end plate which is designed to close the container, an agitator having an agitator shaft which is guided through the end plate into an interior of the container, and an agitator element which is connected to the agitator shaft in the interior of the container, a drive unit which is arranged on the end plate and is coupled to the agitator shaft, and at least one field device which is arranged in the interior and has field device electronics, wherein the end plate comprises: an inner side and an outer side opposite the inner side, an agitator connection device which is designed to guide the agitator shaft through the end plate and to connect the drive unit, at least one field device connection device which is designed to connect the field device on the inner side, and a data transmission unit which is arranged on the outer side and has a motor head piece which can be coupled in terms of signaling to an evaluation unit and is coupled in terms of energy to the drive unit, comprising motor head electronics, and at least one communication unit which is coupled in terms of signaling to the motor head piece, comprising: an adapter piece having adapter electronics which are electrically connected to the field device electronics of the field device, and a communicator piece having communicator electronics which are electrically connected to the adapter electronics and to the motor head electronics, wherein the adapter electronics are configured to communicate signals between the field device electronics and the communicator electronics, wherein the signals carry field device information and measurement information and/or control information, wherein the communicator electronics are configured to communicate the signals between the adapter electronics and the motor head electronics, wherein the data transmission unit also comprises a signal converter which is preferably part of the adapter electronics and/or part of the communicator electronics, wherein the adapter piece and the communicator piece are in the form of separate components which can be coupled to one another, wherein the motor head piece is in the form of a separate component which can be coupled to the communication unit.

One preferred embodiment provides a bioreactor, in particular, for culturing microorganisms and/or cell cultures, having a container, an end plate which is designed to close the container, an agitator having an agitator shaft which is guided through the end plate into an interior of the container, and an agitator element which is connected to the agitator shaft in the interior of the container, a drive unit which is arranged on the end plate and is coupled to the agitator shaft, and at least two field devices which are arranged in the interior and each have field device electronics, wherein the end plate comprises: an inner side and an outer side opposite the inner side, an agitator connection device which is designed to guide the agitator shaft through the end plate and to connect the drive unit, at least two field device connection devices which are designed to each connect one of the field devices on the inner side, and a data transmission unit which is arranged on the outer side and has a motor head piece which can be coupled in terms of signaling to an evaluation unit and is coupled in terms of energy to the drive unit, comprising motor head electronics, and at least two communication units which are each coupled in terms of signaling to the motor head piece, each comprising: an adapter piece having adapter electronics which are electrically connected to the field device electronics of one of the field devices, and a communicator piece having communicator electronics which are electrically connected to the adapter electronics and to the motor head electronics, wherein the adapter electronics are configured to communicate signals between the field device electronics and the communicator electronics, wherein the signals carry field device information and measurement information and/or control information, wherein the communicator electronics are configured to communicate the signals between the adapter electronics and the motor head electronics, wherein the data transmission unit also comprises a signal converter which is preferably part of the adapter electronics and/or part of the communicator electronics, wherein the adapter piece and the communicator piece are in the form of separate components which can be coupled to one another, wherein the motor head piece is in the form of a separate component which can be coupled to the communication units.

The solution described here provides the bioreactor having the end plate and the data transmission unit which is arranged on the outer side of the end plate and makes it possible to transmit signals between the field device(s) and the evaluation unit. Such a bioreactor comprises the container which can be closed by means of the end plate and the interior of which preferably defines a reaction chamber. The bioreactor also comprises the agitator which can be driven by means of the drive unit, in particular, in order to thoroughly mix a culture medium inside the reaction chamber. In order to monitor and/or set desired reaction conditions, the bioreactor also comprises a field device or two or more field devices, in particular, sensors and/or actuators, which is/are arranged in the interior. In this case, the field device(s) is/are arranged at the field device connection devices of the end plate. The data transmission unit is arranged on the outer side of the end plate and is designed to communicate between the field device(s) and the evaluation unit. The data transmission unit comprises the motor head, the at least one adapter piece and the at least one communicator piece. The motor head can preferably be installed on the drive unit.

The bioreactor, in particular, the end plate, may preferably be equipped with different field devices, in particular, with different sensors and/or actuators. A field device may be, for example, in the form of a sensor, an actuator or another component of a bioreactor. The bioreactor may preferably comprise field devices in order to monitor parameters which can preferably be captured while culturing bacterial, animal, and human cells. Such parameters may preferably be the temperature, pH value, dissolved oxygen content, and actual values of actuators, for example, pumps, agitators, Peltier coolers, light rods, and/or a gas introduction system. In addition, further field devices may be provided in order to determine data, for example, density of living cells, nutrient concentration and/or metabolite concentration. A field device in the form of a sensor may be, for example, in the form of a pH sensor, a redox potential sensor, a temperature sensor, a dissolved oxygen content sensor, etc. A field device in the form of an actuator may be, for example, in the form of a pump, an agitator, a Peltier cooler, and/or a light rod etc.

In accordance with the field devices, it is possible to select and/or produce a suitable adapter piece, the adapter piece electronics of which are designed to receive signals from the field device and/or to transmit signals to this field device.

The communicator electronics of a communicator piece are electrically connected to the motor head electronics in order to receive signals from a field device, in particular, via an adapter piece, and to transmit these signals to the motor head electronics and/or to receive signals from the motor head electronics and to transmit them to the field device, in particular via an adapter piece. As a result, the motor head electronics can receive signals from the individual field devices and/or transmit signals to the latter.

The signal converter is designed to convert the signals. The signal converter may preferably be part of the adapter electronics and/or part of the communicator electronics and/or both the adapter electronics and the communicator electronics may each comprise a signal converter.

Analog signals from a field device are preferably first of all converted into standardized signals (for example, 0 V to 4.095 V) and are then converted into digital signals (for example, 0 to 4095). This conversion is preferably carried out in the communication unit, in particular, in the adapter electronics and/or in the communicator electronics. The adapter piece electronics may preferably be designed to receive signals from the communicator electronics, to convert them by means of the signal converter and to transmit them to the adapter electronics. For example, the signals may be completely converted in the adapter electronics. The signals may also be completely converted in the communicator electronics. The signals may also be partially converted in the adapter electronics and partially converted in the communicator electronics. For example, analog signals from a field device may be converted into analog standardized signals in the adapter electronics and the analog standardized signals may be converted into digital signals in the communicator electronics.

As a result of different adapter pieces which are configured in accordance with the field devices, the bioreactor can be individually adapted to customer requirements. Particularly preferably, the bioreactor can be individually produced for customer requirements.

This configuration makes it possible to achieve a particularly advantageous design of the bioreactor. In particular, cabling on the bioreactor can be reduced. This results overall in tidier laboratory workstations and simpler handling of the bioreactor.

Configurations are also possible in which a common communicator piece is provided for two or more field devices each having an associated adapter piece. In such a configuration, the communicator piece, in particular, the communicator electronics, is then preferably designed to communicate with the adapter electronics of two or more adapter pieces.

The drive unit may preferably comprise drive electronics which are designed to communicate with the motor head electronics. The drive electronics and the motor head electronics may preferably be electrically connected to one another in a wireless manner, in particular, via radio, or via a cable. In particular, energy may be supplied with contact, preferably in a wired manner, or wirelessly, in particular, inductively. The preferred inductive energy supply may preferably be supplied by an inductive source in the motor head piece.

The drive electronics are preferably designed to control the drive unit. The drive electronics may preferably be arranged in a manner spatially separate from the drive unit. For example, the drive electronics may be arranged together with the evaluation unit and/or a control unit.

The motor head may be coupled in terms of energy, for example, to the drive unit in order to supply it with energy. The drive unit may also be supplied with energy independently of the motor head.

The agitator comprises the agitator shaft which is guided through the end plate into the interior and has agitator elements. The agitator shaft is coupled to the drive unit arranged on the end plate. The drive unit may preferably act at an upper end of the agitator shaft. The agitator shaft may preferably be mounted in a bearing so as to be rotatable about an axis of rotation. In particular, the agitator elements may be fastened to the agitator shaft in a torsionally rigid manner.

The agitator shaft may preferably be arranged in a substantially vertical manner and, with the agitator elements, may form the agitator. The agitator elements may preferably each move in a horizontal plane. Particularly preferably, the agitator elements may have an inclination with respect to the vertical, in particular, with respect to the agitator shaft. The agitator elements may preferably have different inclinations with respect to the vertical, in particular, with respect to the agitator shaft. The bioreactor may preferably also have two or more agitators.

The container may preferably be formed from plastic or glass. Particularly preferably, the container may have a dimensionally stable design. The container may preferably have a base and a wall surrounding the base. This configuration makes it possible to clean and sterilize the container in order to be able to be reused.

The bioreactor may preferably also be in the form of a single-use bioreactor. The container may be, in particular, flexible, preferably in the form of a bag. This configuration makes it possible to avoid the need for complicated sterilization and cleaning processes. Furthermore, the risk of a distorted or unusable result on account of incomplete sterilization and a resulting disruption of a process can be reduced, in particular, avoided.

The container may preferably have a feed device for supplying starting materials and a removal opening for removing an end product and/or a sample. The feed device may preferably be arranged in an upper region of the container and the removal opening may be arranged in a lower region of the container.

The evaluation unit may particularly preferably be in the form of a reactor controller. The reactor controller may preferably collect the data from the field devices, preferably visualize and preferably store said data. These data may preferably also be stored together with process data in a central database. As a result, the data may be available, in particular, for process development within the reactor controller and may preferably be used for monitoring and/or process control. In particular, the data may be evaluated and used to control actuators on the basis of the captured data.

For further advantages, embodiment variants and embodiment details of this first aspect and its possible developments, reference is also made to the description below of the corresponding features and developments of the second and third aspects.

According to a second aspect, the object mentioned at the outset is achieved by means of an end plate for closing a bioreactor, comprising an inner side and an outer side opposite the inner side, an agitator connection device which is designed to guide an agitator shaft through the end plate and to connect a drive unit which can be coupled to the agitator shaft, at least one field device connection device which is designed to connect a field device on the inner side, a data transmission unit which is arranged on the outer side and has a motor head piece which can be coupled in terms of signaling to an evaluation unit and can be coupled in terms of energy to the drive unit which can be arranged on an end plate of a bioreactor, comprising motor head electronics, and at least one communication unit which is coupled in terms of signaling to the motor head piece, comprising: an adapter piece having adapter electronics which can be electrically connected to field device electronics of the field device, and a communicator piece having communicator electronics which are electrically connected to the adapter electronics and to the motor head electronics, wherein the adapter electronics are configured to communicate signals between the field device electronics and the communicator electronics, wherein the signals carry field device information and measurement information and/or control information, wherein the communicator electronics are configured to communicate the signals between the adapter electronics and the motor head electronics, wherein the data transmission unit also comprises a signal converter which is preferably part of the adapter electronics and/or part of the communicator electronics, wherein the adapter piece and the communicator piece are in the form of separate components which can be coupled to one another, wherein the motor head piece is in the form of a separate component which can be coupled to the communication unit.

An end plate for closing a bioreactor is preferably provided, comprising an inner side and an outer side opposite the inner side, an agitator connection device which is designed to guide an agitator shaft through the end plate and to connect a drive unit which can be coupled to the agitator shaft, at least two field device connection devices which are designed to respectively connect a field device on the inner side, a data transmission unit which is arranged on the outer side and has a motor head piece which can be coupled in terms of signaling to an evaluation unit and can be coupled in terms of energy to the drive unit which can be arranged on an end plate of a bioreactor, comprising motor head electronics, and at least two communication units which are each coupled in terms of signaling to the motor head piece, each comprising: an adapter piece having adapter electronics which can be electrically connected to field device electronics of one of the field devices, and a communicator piece having communicator electronics which are electrically connected to the adapter electronics and to the motor head electronics, wherein the adapter electronics are configured to communicate signals between the field device electronics and the communicator electronics, wherein the signals carry field device information and measurement information and/or control information, wherein the communicator electronics are configured to communicate the signals between the adapter electronics and the motor head electronics, wherein the adapter piece and the communicator piece are in the form of separate components which can be coupled to one another, wherein the data transmission unit also comprises a signal converter which is preferably part of the adapter electronics and/or part of the communicator electronics, wherein the motor head piece is in the form of a separate component which can be coupled to the communication units.

The solution described here provides the end plate for closing the bioreactor and the data transmission unit which is arranged on the outer side of the end plate and makes it possible to transmit signals between the field device(s) which can be connected and the evaluation unit which can be coupled in terms of signaling. Such an end plate has the inner side and the outer side. The end plate may preferably be fitted and fastened to a container of the bioreactor in such a manner that the inner side faces an interior of the container and bounds the interior. The outer side may preferably be formed opposite the inner side and, in particular, may face away from the interior of the container. The end plate also comprises the agitator connection device in order to fasten an agitator to the agitator shaft on the end plate and to connect the drive unit to the agitator shaft. In addition, the end plate has (a) field device connection device(s) in order to connect one or more field devices, in particular sensors and/or actuators, to the end plate.

The field device connection devices may preferably be all devices for fastening field devices. In particular, the field devices may be fastened to these field device connection devices in a form-fitting and/or force-fitting manner.

A field device connection device may preferably have a membrane which closes, preferably seals, the interior. The membrane may be designed to guide a field device from outside the bioreactor through the membrane and to insert it into the interior. As a result of the sterility which is achieved by providing a membrane, bioreactors can be equipped and/or upgraded and/or retrofitted particularly easily with field devices as required. Furthermore, this makes it possible to replace field devices particularly easily in the event of a defect.

For further advantages, embodiment variants and embodiment details of this second aspect and its possible developments, reference is also made to the description below of the corresponding features and developments of the third aspect and to the description above of the corresponding features and developments of the first aspect.

According to a third aspect, the object mentioned at the outset is achieved by means of a data transmission unit for an end plate of a bioreactor, having a motor head piece which can be coupled in terms of signaling to an evaluation unit and can be coupled in terms of energy to a drive unit which can be arranged on an end plate of a bioreactor, comprising motor head electronics, and at least one communication unit which is coupled in terms of signaling to the motor head piece, comprising: an adapter piece having adapter electronics which can be electrically connected to field device electronics of a field device, and a communicator piece having communicator electronics which are electrically connected to the adapter electronics and to the motor head electronics, wherein the adapter electronics are configured to communicate signals between the field device electronics and the communicator electronics, wherein the signals carry field device information and measurement information and/or control information, wherein the communicator electronics are configured to communicate the signals between the adapter electronics and the motor head electronics, wherein the data transmission unit also comprises a signal converter which is preferably part of the adapter electronics and/or part of the communicator electronics, wherein the adapter piece and the communicator piece are in the form of separate components which can be coupled to one another, wherein the motor head piece is in the form of a separate component which can be coupled to the communication unit.

A data transmission unit for an end plate of a bioreactor is preferably provided, having a motor head piece which can be coupled in terms of signaling to an evaluation unit and can be coupled in terms of energy to a drive unit which can be arranged on an end plate of a bioreactor, comprising motor head electronics, and at least two communication units which are each coupled in terms of signaling to the motor head piece, each comprising: an adapter piece having adapter electronics which can be electrically connected to field device electronics of a field device, and a communicator piece having communicator electronics which are electrically connected to the adapter electronics and to the motor head electronics, wherein the adapter electronics are configured to communicate signals between the field device electronics and the communicator electronics, wherein the signals carry field device information and measurement information and/or control information, wherein the communicator electronics are configured to communicate the signals between the adapter electronics and the motor head electronics, wherein the data transmission unit also comprises a signal converter which is preferably part of the adapter electronics and/or part of the communicator electronics, wherein the adapter piece and the communicator piece are in the form of separate components which can be coupled to one another, wherein the motor head piece is in the form of a separate component which can be coupled to the communication units.

The invention is based, inter alia, on the knowledge that the signals from the field devices, in particular, sensor signals, are often susceptible to interference. Field devices which are designed to transmit and/or receive analog signals are usually used. Analog signals may be particularly susceptible to interference. For this reason, transmission of these signals using long cables, preferably using cables with a length of at least 100 cm, may be disadvantageous, in particular.

The invention is also based on the knowledge that, in known solutions, each field device is often individually connected to an evaluation unit via a cable in order to transmit a signal. If more than a single field device is used, the cabling of the individual field devices may lead to confusion and may have an adverse effect on the manageability, in particular, of the data transmission unit, preferably during installation and/or during use. In addition, the direct connection of a field device to the evaluation unit results in an appropriate module or corresponding evaluation electronics having to be developed for each field device in order to be able to receive and evaluate signals from the various field devices and/or to be able to transmit signals to the various field devices. For this reason, in previously known solutions, the corresponding evaluation electronics or an appropriate module must be developed when using a new field device. This can often result in longer waiting times before using the new field devices.

The solution described here provides a data transmission unit having the motor head piece and at least one communication unit, preferably having at least two communication units. A communication unit comprises the adapter piece and the communicator piece. Coupling the motor head piece in terms of signaling to the evaluation unit and coupling the respective adapter piece in terms of signaling to the field device makes it possible to robustly transmit signals between the field device and the evaluation unit by means of the data transmission unit.

Depending on the field devices which are intended to be used, a specially configured adapter piece may preferably be selected and/or produced for each field device. These adapter pieces each comprise adapter electronics which are designed to receive signals from the corresponding field device and/or to transmit signals to this field device.

Different field devices are generally configured to transmit different signals which carry field device information and measurement information, and/or to receive different signals which carry control information. For example, field devices may transmit and/or receive digital or analog signals. In particular, field devices may transmit and/or generate signals in a particular frequency range or in the DC range. For this reason, it is advantageous to use accordingly configured adapter pieces in order to be able to convert these signals and to transmit them to the communicator piece and/or in order to be able to receive these signals from the communicator piece, to convert them and to transmit them to the field device.

Transmitting signals which carry field device information and measurement information makes it possible to transmit measurement data, which have been captured with the aid of the field device, and preferably data relating to the field device, for example an item of information relating to which field device is used to capture these measurement data, to the communicator piece. The field device information may preferably communicate a field device type to the communicator electronics.

Communicating the field device type makes it possible to transmit properties of the field device. These properties may comprise a sensor type and/or an actuator type and whether these signals are digital or analog and/or the like.

Receiving signals which carry control information and transmitting these signals to the field device makes it possible to control the latter. In particular, the field device can be activated and/or deactivated and/or adjusted and/or calibrated thereby.

In contrast to the adapter piece, the communicator piece may preferably have an identical design for each communication unit. The communicator pieces may therefore preferably have a standard configuration. The communicator electronics of each communicator piece are electrically connected to the motor head electronics in order to receive signals from the field device via the adapter piece and to transmit said signals to the motor head electronics and/or to receive signals from the motor head electronics and to transmit said signals to the field device via the adapter piece. As a result, the motor head electronics can receive signals from the individual field devices and/or can transmit signals to the latter.

In this case, the motor head piece can be coupled at least in terms of signaling to the evaluation unit. In particular, the motor head electronics may be electrically connected to evaluation electronics of the evaluation unit. The motor head piece may preferably be designed to be coupled in terms of energy to the evaluation unit. As a result, the evaluation unit can preferably also supply the motor head electronics with energy.

The motor head piece is connected at least in terms of energy to the drive unit and is designed to supply the drive unit with energy. In particular, the motor head electronics may be electrically connected to drive electronics of the drive unit. The motor head piece may preferably be designed to be coupled in terms of signaling to the drive unit.

Coupling of two components in terms of signaling and/or in terms of energy may preferably be understood as meaning the fact that the corresponding electronics of these components are electrically connected to one another and are preferably designed to transmit signals and/or energy. Transmission of signals and/or energy may preferably be understood as meaning the transmission and/or reception of signals and/or energy.

The motor head piece, the adapter pieces, and the communicator pieces are each separate components which can be coupled to one another. Each communicator piece can preferably be combined with the adapter pieces.

The data transmission unit can be individually adapted to customer requirements by virtue of different adapter pieces which are configured in accordance with the field devices.

As a result of the proposed solution, there is no need for the evaluation unit to comprise separate evaluation electronics for each field device. Transmitting signals, preferably standardized signals, which carry measurement information and field device information makes it possible, in particular, to evaluate the signals, which are transmitted via the various communication units and the motor head piece, preferably using a single set of evaluation electronics.

As a result of the proposed solution with adapted adapter pieces, only an accordingly configured adapter piece must be designed on the hardware side—the hardware outlay involved in integrating a new field device in a system is therefore considerably lower.

The processing of the signals may be made more robust by using the adapter piece in the immediate vicinity of the field device and, in particular, by converting signals into analog and/or digital signals which are less susceptible directly at the location at which they are produced.

The advantage of this solution is also the fact that the adapter piece makes it possible to achieve a type of standardization which results in simplification of the processing of the signals. In addition, components which are needed to condition the signals can be reduced.

The motor head may preferably be electrically connectable or connected to a feeder cable. The feeder cable may preferably comprise, in addition to any wires for supplying energy to the drive unit, four wires, two for supplying energy, in particular, to the motor head electronics, and two for transmitting data. The wires for transmitting data may correspond to the RS485 standard, for example. This enables communication which is particularly robust and not susceptible to errors.

The motor head electronics may preferably be designed to transmit signals to the evaluation unit or to receive signals from the latter using Modbus, for example. The motor head electronics may also be designed to operate, during bridge operation, between the field devices and the evaluation unit or a control unit and additionally as a hub for field devices on a bioreactor.

Particularly preferably, the data transmission unit may comprise the evaluation unit, wherein the evaluation unit is coupled in terms of signaling to the motor head piece.

The evaluation unit may preferably be designed to receive signals, preferably from the data transmission unit, and to evaluate them. The evaluation unit may also be designed to generate signals and to transmit them to the data transmission unit. These signals may preferably be used to control and/or calibrate the field devices. Particularly preferably, the evaluation unit may receive signals from the data transmission unit, may evaluate these signals and, on the basis of these signals, may generate signals and transmit them to the data transmission unit.

The evaluation unit may preferably have a user interface which makes it possible for operating personnel to operate the data transmission unit. As a result, field devices can be controlled and/or data can be read out, preferably manually. Furthermore, the drive unit may preferably be controlled by the operating personnel thereby.

The data transmission unit for an end plate of a bioreactor may preferably have the motor head piece which can be coupled in terms of signaling to an evaluation unit and can be coupled in terms of energy to a drive unit which can be arranged on an end plate of a bioreactor, comprising motor head electronics, and a single communication unit coupled in terms of signaling to the motor head piece, comprising: an adapter piece having adapter electronics which can be electrically connected to field device electronics of a field device, and a communicator piece having communicator electronics which are electrically connected to the adapter electronics and to the motor head electronics, wherein the adapter electronics comprise a signal converter and are configured to communicate signals between the field device electronics and the communicator electronics, wherein the signals carry field device information and measurement information and/or control information, wherein the communicator electronics are configured to communicate the signals between the adapter electronics and the motor head electronics, wherein the adapter piece and the communicator piece are in the form of separate components which can be coupled to one another, wherein the motor head piece is in the form of a separate component which can be coupled to the communication unit.

According to one preferred development of the data transmission unit, the adapter piece comprises a field device interface and a communicator interface, wherein the adapter electronics are connected between the field device interface and the communicator interface, can be electrically connected to the field device electronics via the field device interface, and are electrically connected to the communicator electronics via the communicator interface, and the communicator piece comprises an adapter interface and a motor head interface, wherein the communicator electronics are connected between the adapter interface and the motor head interface, are electrically connected to the adapter electronics via the adapter interface, and are electrically connected to the motor head electronics via the motor head interface.

The adapter electronics may preferably be designed to transmit and/or receive signals via the field device interface and/or the communicator interface. In this case, the adapter electronics may be designed, in particular, to convert signals from the field device interface into signals of the communicator interface. Furthermore, the adapter electronics may be designed, in particular, to convert signals from the communicator interface into signals of the field device interface.

The communicator electronics may preferably be designed to transmit and/or receive signals via the adapter interface and/or the motor head interface. In this case, the communicator electronics may be designed, in particular, to convert signals from the adapter interface into signals of the motor head interface. Furthermore, the communicator electronics may be designed, in particular, to convert signals from the motor head interface into signals of the adapter interface.

The field device interface and/or the communicator interface and/or the adapter interface and/or the motor head interface may preferably be hardware interfaces which are designed to connect physical systems in electrical engineering and electronics to one another. As a result, the individual components can preferably be connected to one another, in particular the electronics of the individual components can be electrically connected to one another.

The field device interface and/or the communicator interface and/or the adapter interface and/or the motor head interface may preferably be in the form of analog and/or digital interfaces. In particular, the field device interface and/or the communicator interface and/or the adapter interface and/or the motor head interface may be in the form of USB, FireWire, EIA-232, PCI-Express, SPI, I2C, RS232, RS485, DMX, Serial ATA, or Profibus. Particularly preferably, the field device interface and/or the communicator interface and/or the adapter interface and/or the motor head interface may be in the form of an RS485 interface.

The adapter electronics may preferably be accommodated on a printed circuit board. The printed circuit board may preferably have pins. The printed circuit board may preferably have at least two pins which are configured to enable an electrical connection between the adapter electronics and the field device electronics, wherein these pins are preferably configured as outputs and/or inputs. In addition, the printed circuit board may preferably have two pins which are configured to supply energy. The printed circuit board may have, in particular, two spring contacts which enable an electrical connection between the adapter electronics and the communicator electronics.

Further configured pins may be hard-coded on the printed circuit board of the adapter electronics and may forward corresponding bit patterns to the communicator electronics. Alternatively or additionally, this forwarding may also be carried out using a corresponding protocol, wherein digital signals are then preferably already present in the adapter electronics.

The communicator electronics may also be preferably accommodated on a printed circuit board and/or the motor head electronics may be accommodated on a printed circuit board.

Particularly preferably, the data transmission unit comprises at least one first group of first adapter pieces and one second group of second adapter pieces, wherein the adapter electronics of the first adapter pieces are designed to communicate the signals between the field device electronics of a first field device and the communicator electronics, wherein the adapter electronics of the second adapter pieces are designed to communicate the signals between the field device electronics of a second field device and the communicator electronics, wherein the adapter piece of each communication unit is selected from at least the first group of first adapter pieces and the second group of second adapter pieces on the basis of a field device to be coupled.

This preferred embodiment provides a modular system. This system preferably comprises different groups of adapter pieces which are preferably configured in accordance with different field devices. The adapter pieces may be selected, in particular, on the basis of a field device and may be coupled to the latter. This makes it possible to use different field devices.

The communicator pieces may preferably be substantially identical and may be designed to be coupled to each of the adapter pieces.

In particular, this makes it possible to provide a data transmission unit which is individually adapted to customer requirements. It is also advantageous that a data processing unit can also be retrofitted and/or upgraded.

According to a further preferred embodiment variant, the adapter piece comprises a field device coupling which is designed to connect the field device to the adapter piece mechanically, preferably releasably. Particularly preferably, the adapter piece may be screwed onto the field device.

The field device coupling may preferably be formed at the field device interface. Particularly preferably, the field device can be connected to the adapter piece both electrically and mechanically as a result.

This makes it possible to connect the adapter piece to the field device in a particularly simple manner. Furthermore, the mechanical connection of these components enables a particularly compact field device/adapter piece unit which enables simple handling.

The releasable connection of the adapter piece to the field device may preferably make it possible to replace the field device and/or the adapter piece.

It is also preferred for the communicator piece to comprise an adapter coupling which is designed to connect the adapter piece to the communicator piece mechanically, preferably releasably.

The adapter coupling may preferably be formed at the adapter interface. Particularly preferably, the communicator piece may be connected to the adapter piece both electrically and mechanically as a result.

This makes it possible to connect the communicator piece to the adapter piece in a particularly simple manner. Furthermore, the mechanical connection of these components enables a particularly compact communicator piece/adapter piece unit which enables simple handling.

The releasable connection of the communicator piece to the adapter piece may preferably make it possible to replace the communicator piece and/or the adapter piece.

In particular, it is preferred for the adapter piece to comprise a field device coupling which is designed to connect the field device to the adapter piece mechanically, preferably releasably, and/or for the communicator piece to comprise an adapter coupling which is designed to connect the adapter piece to the communicator piece mechanically, preferably releasably.

Particularly preferably, the field device coupling may be designed to connect the field device to the adapter piece by means of a bayonet, screw or click connection. The field device coupling may preferably be formed on an adapter piece housing. In particular, the field device may have an adapter coupling which is designed to be brought into engagement with the field device coupling.

Particularly preferably, the adapter coupling may be designed to connect the communicator piece to the adapter piece by means of a bayonet, screw or click connection. The adapter coupling may preferably be formed on a communicator piece housing. In particular, the adapter piece may have a communicator coupling which is designed to be brought into engagement with the adapter coupling.

According to a further preferred embodiment variant, the signal converter is an analog/digital converter. Furthermore, the adapter electronics and/or the communicator electronics and/or the signal converter is/are preferably configured to receive analog signals, to convert them into standardized analog signals and to convert the standardized analog signals into digital signals and to transmit the digital signals and/or vice versa.

This embodiment variant makes it possible for analog signals which are preferably generated by the field device electronics and are transmitted to the adapter electronics to be converted into digital signals in the adapter electronics and/or the communicator electronics. Digital signals are generally less susceptible to interference during transmission since signal levels of the digital signals can still be assigned to a correct value with a certain tolerance. In particular, differential digital signals are particularly robust here with respect to external interference.

The communicator electronics may preferably comprise a repeater and/or a signal conditioner and may be designed to receive digital signals, to condition the signals by means of the repeater and/or the signal conditioner and to transmit the conditioned digital signals. This makes it possible to correct errors, if necessary, in particular, to remove unwanted noise. The advantage of this is that, as a result of the conditioning of the digital signals in the communicator electronics, only the useful signal can preferably be transmitted on to the motor head electronics.

In particular, the motor head electronics may also comprise a repeater and/or a signal conditioner in order to condition the digital signals received from the communicator pieces.

The conversion of analog signals into digital signals may make it possible to transmit signals in a more robust manner.

The signal converter may preferably also comprise a repeater and/or a signal conditioner which is configured to condition digital signals. This embodiment variant is advantageous, in particular, when the adapter piece is configured to receive digital signals from the field device and/or to receive digital signals from the communicator piece and to transmit them to the field device.

For analog transmission, it is preferably possible to use current signals, in particular 0 mA-20 mA or with an offset zero point 4 mA-20 mA, or voltage signals, in particular <0 V-5 V, 0 V-10 V, with an offset zero point 1 V-5 V, with an offset zero point 2 V-10 V or with or without an offset zero point −10 V-10 V.

Particularly preferably, the current signals can be used as standardized signals. These are particularly insensitive to electromagnetic interference and voltage losses.

In particular, analog sensor signals from the field device may be converted into standardized signals (for example 0 V to 4.095 V) and forwarded as converted digital signals (for example 0-4095).

It is also preferred if the communicator electronics and/or the motor head electronics are configured to receive the signals without or with contact, preferably in a wired manner, to convert the signals into radio signals and to transmit them by radio or in a wired manner and/or vice versa. This makes it possible to wirelessly transmit the signals between the communicator electronics and the motor head electronics. This configuration makes it possible to reduce or avoid cabling on the data transmission unit. This also particularly simplifies the manageability and, in particular, the process of fitting the data transmission unit, in particular, to the end plate of the bioreactor.

According to this embodiment variant, the communicator piece and/or the motor head piece may have an antenna which is configured to transmit and/or receive the radio signals. The antenna may preferably be flexible. This makes it possible to achieve the best possible closure of the fields between the motor head piece and the communicator piece.

The conversion into radio signals may be carried out using modulation, for example. In particular, the original signal or the information in the original signal can be recovered by means of demodulation and possibly forwarded and/or processed further.

As a result of this embodiment variant, there is no need to lay any electrical cables between the communicator piece and the motor head piece.

It is also preferred if the adapter electronics are configured to receive the signals without or with contact, preferably in a wired manner, to convert the signals into radio signals and to transmit them by radio or in a wired manner and/or vice versa. This makes it possible to wirelessly transmit the signals between the adapter electronics and the communicator electronics. This configuration makes it possible to reduce or avoid cabling on the data transmission unit. This also particularly simplifies the manageability and, in particular, the process of fitting the data transmission unit, in particular to the end plate of the bioreactor.

According to this embodiment variant, the communicator piece and/or the adapter piece may have an antenna which is configured to transmit and/or receive the radio signals. The antenna may preferably be flexible. This makes it possible to achieve the best possible closure of the fields between the adapter piece and the communicator piece. A further possible form is an integrated antenna on the printed circuit board of the communicator electronics and/or on the printed circuit board of the adapter electronics.

The conversion into radio signals may be carried out using modulation, for example. In particular, the original signal or the information in the original signal can be recovered by means of demodulation and possibly forwarded and/or processed further.

As a result of this embodiment variant, there is no need to lay any electrical cables between the communicator piece and the adapter piece.

A modem can be used to convert to signals, preferably the digital signals, into radio signals and/or vice versa. The communicator electronics and/or the adapter electronics may preferably have the modem which is configured to convert digital signals into radio signals and/or vice versa.

The adapter electronics and/or the communicator electronics may preferably also be designed to receive radio signals, to convert them into original digital signals and to transmit the original digital signals.

The signals may preferably be transmitted between the adapter electronics and the communicator electronics with contact, preferably in a wired manner, or via radio, and/or vice versa. Particularly preferably, the signals may be transmitted between the communicator electronics and the motor head electronics with contact, preferably in a wired manner, or via radio, and/or vice versa.

Radio signals may generally preferably be based on a Bluetooth protocol or a protocol modified therefrom, in particular Bluetooth Low Energy, ZigBee, 6LoWPAN, and/or a (different) wireless protocol. In particular, a radio connection with a very short range and therefore a low transmission power can be effected.

A wired connection can generally preferably be implemented by means of a very short, in particular, semi-flexible, cable. In particular, it is possible to use a cable which is fastened to the communicator by means of a connector which is to be fixed, preferably is to be fixed by screwing. For example, an opposite side of the cable could be coupled to the motor head piece or to the adapter piece, preferably by means of a connector, for example a connector tapering in a wedge-shaped manner, and/or in the form of a spring contact. The connection between the cable and the motor head is preferably releasably secured, for example, by means of a latching connection and/or a magnetic connection. This makes it possible to ensure, on the one hand, fast and simple coupling and, on the other hand, manual release of a lock achieved by means of the latching mechanism.

According to one particularly preferred embodiment variant, the data transmission unit may have the motor head piece which can be coupled in terms of signaling to the evaluation unit and can be coupled in terms of energy to the drive unit which can be arranged on the end plate of the bioreactor, comprising the motor head electronics, and the at least two communication units which are each coupled in terms of signaling to the motor head piece, each comprising: the adapter piece having the adapter electronics which can be electrically connected to the field device electronics of the field device, and the communicator piece having the communicator electronics which are electrically connected to the adapter electronics and to the motor head electronics, wherein the adapter electronics comprise the analog/digital converter and are configured to receive analog signals, to convert them into digital signals and to transmit the digital signals and/or vice versa in order to communicate the signals between the field device electronics and the communicator electronics, wherein the signals carry field device information and measurement information and/or control information, wherein the communicator electronics are configured to communicate the signals between the adapter electronics and the motor head electronics, wherein the adapter piece and the communicator piece are in the form of separate components which can be coupled to one another, wherein the motor head piece is in the form of a separate component which can be coupled to the communication units.

This configuration makes it possible to use field devices which generate analog and, in particular, particularly susceptible signals and transmit these signals to the adapter piece. This makes it possible to connect the adapter pieces to conventional field devices which cannot generate digital signals.

Signal transmission, in particular, more robust signal transmission, can be enabled by converting this signal at the location at which it is produced. The digital signals are clearer than analog signals and are accurately defined. These signals can therefore also be reconstructed more easily, have a high degree of interference immunity and enable flexible further processing.

According to an alternative particularly preferred embodiment variant, the data transmission unit may have the motor head piece which can be coupled in terms of signaling to the evaluation unit and can be coupled in terms of energy to the drive unit which can be arranged on the end plate of the bioreactor, comprising the motor head electronics, and the at least two communication units which are each coupled in terms of signaling to the motor head piece, each comprising: the adapter piece having the adapter electronics which can be electrically connected to the field device electronics of the field device, and the communicator piece having the communicator electronics which are electrically connected to the adapter electronics and to the motor head electronics, wherein the adapter electronics comprise the analog/digital converter and are configured to receive analog signals, to convert them into standardized signals and to transmit the standardized signals and/or vice versa in order to communicate the signals between the field device electronics and the communicator electronics, wherein the signals carry field device information and measurement information and/or control information, wherein the communicator electronics are configured to communicate the signals between the adapter electronics and the motor head electronics, wherein the adapter piece and the communicator piece are in the form of separate components which can be coupled to one another, wherein the motor head piece is in the form of a separate component which can be coupled to the communication units.

This configuration makes it possible to use field devices which generate analog and, in particular, particularly susceptible signals and transmit these signals to the adapter piece. This makes it possible to connect the adapter pieces to conventional field devices which cannot generate digital signals.

As a result of the conversion of the signals from the field device into standard signals, the latter can be forwarded and processed. In addition, on account of the standardization, it is possible to use standardized communicator pieces which can communicate with different adapter pieces.

Particularly preferably, current signals can be used as standardized signals. These are particularly insensitive to electromagnetic interference and voltage losses. This makes it possible to transmit signals in a more robust manner. Furthermore, the analog/digital converter itself can be permanently supplied with energy as a result.

According to an alternative particularly preferred embodiment variant, the data transmission unit may have the motor head piece which can be coupled in terms of signaling to the evaluation unit and can be coupled in terms of energy to the drive unit which can be arranged on the end plate of the bioreactor, comprising the motor head electronics, and the at least two communication units which are each coupled in terms of signaling to the motor head piece, each comprising: the adapter piece having the adapter electronics which can be electrically connected to the field device electronics of the field device, and the communicator piece having the communicator electronics which are electrically connected to the adapter electronics and to the motor head electronics, wherein the adapter electronics comprise the signal converter, preferably the analog/digital converter, and are configured to communicate signals between the field device electronics and the communicator electronics, preferably in order to receive analog signals, to convert them into standardized signals and to transmit the standardized signals and/or vice versa, wherein the signals carry field device information and measurement information and/or control information, wherein the communicator electronics comprise the analog/digital converter and are configured to receive analog signals, to convert them into digital signals and to transmit the digital signals and/or vice versa in order to communicate the signals between the adapter electronics and the motor head electronics, wherein the adapter piece and the communicator piece are in the form of separate components which can be coupled to one another, wherein the motor head piece is in the form of a separate component which can be coupled to the communication units.

Each of the particularly preferred embodiment variants above ensures more robust signal transmission. In bioprocess technology, robust signal transmission and, associated with this, exact transmission of the information is extremely important. When culturing microorganisms and/or cell cultures, each individual parameter is decisively important. For example, the composition of the culture medium, its pH value, and temperature are particularly important. Even slight fluctuations may therefore affect the growth curve. In addition, it should be remembered that the microorganisms and/or cell cultures consume nutrients of the culture medium. It is therefore necessary to exactly monitor the nutrient concentrations, preferably in real time, in order to be able to regulate a supply of nutrients. Furthermore, microorganisms and/or cell cultures may result in different foaming as a result of the metabolism. In particular, in order to avoid excessive foaming which may also result in overflowing of the bioreactor, the foaming must be monitored in real time in order to control this by adjusting other parameters.

According to an alternative particularly preferred embodiment variant, the data transmission unit may have the motor head piece which can be coupled in terms of signaling to the evaluation unit and can be coupled in terms of energy to the drive unit which can be arranged on the end plate of the bioreactor, comprising the motor head electronics, and the at least two communication units which are each coupled in terms of signaling to the motor head piece, each comprising: the adapter piece having the adapter electronics which can be electrically connected to the field device electronics of the field device, and the communicator piece having the communicator electronics which are electrically connected to the adapter electronics and to the motor head electronics, wherein the adapter electronics comprise the signal converter and are configured to communicate the signals between the field device electronics and the communicator electronics, wherein the signals carry field device information and measurement information and/or control information, wherein the communicator electronics are configured to receive the signals with contact, preferably in a wired manner, to convert the signals into radio signals and to transmit them by radio and/or vice versa in order to communicate the signals between the adapter electronics and the motor head electronics, wherein the adapter piece and the communicator piece are in the form of separate components which can be coupled to one another, wherein the motor head piece is in the form of a separate component which can be coupled to the communication units.

According to this preferred configuration, the signal converter may preferably be an analog/digital converter or a repeater and/or a signal conditioner. In particular, if the adapter piece can be connected to an analog sensor, the signal converter may be in the form of an analog/digital converter. In particular, if the adapter piece can be connected to a digital sensor, the signal converter may be in the form of a repeater and/or a signal conditioner.

Alternatively, the signal converter may be an analog/digital converter, for example. In this case, the communicator electronics may comprise an analog/digital converter and may be configured to receive standardized analog signals, to convert them into digital signals and to convert the digital signals into radio signals.

This preferred embodiment variant combines the above-mentioned advantages with regard to the different configuration of the signal converters and the advantages of radio transmission. In particular, this makes it possible to reduce or avoid cabling on the data transmission unit. This also particularly simplifies the manageability and, in particular, the process of fitting the data transmission unit, in particular to the end plate of the bioreactor.

According to a further preferred embodiment variant, provision is made for the field device interface and/or the communicator interface and/or the adapter interface and/or the motor head interface to be in the form of a connection on a cable, wherein the cable preferably has a length of at most 20 cm.

The connection may be in the form of a connector arranged on a cable, in particular.

The cable may preferably have a maximum length of 50 cm, 20 cm, 15 cm, 10 cm, 8 cm, 6 cm, 5 cm or 4 cm. The maximum length of the cable is preferably dependent on the dimensions of the bioreactor.

The cables having a particularly short length make it possible, on the one hand, to improve the manageability since no unnecessary long cables are used and cabling is therefore reduced. This may preferably also result in a tidy external appearance. In addition, the signal transmission can be improved.

It is particularly preferred that the motor head piece is coupled in terms of energy to the communicator piece, wherein the motor head electronics are configured to supply the communicator electronics with energy, in particular power, and/or the communicator piece is coupled in terms of energy to the adapter piece, wherein the communicator electronics are configured to supply the adapter electronics with energy, in particular power, and/or the adapter piece can be coupled in terms of energy to the field device, wherein the adapter electronics are configured to supply the field device electronics with energy, in particular, power, wherein the power is preferably transmitted with contact, preferably in a wired manner, and/or inductively.

The preferred inductive energy supply may preferably be supplied by an inductive source in the motor head piece.

The motor head electronics and/or the communicator electronics and/or the adapter electronics may preferably comprise supply electronics. The motor head piece may be configured, in particular, as a power distributor in order to supply all communicator electronics electrically connected to the motor head electronics with power. This makes it possible to ensure a particularly simple design of the data transmission unit. In particular, the individual components, that is to say preferably the adapter piece and/or the communicator piece, may have a particularly simple configuration. This also dispenses with the need to electrically connect the individual components to a supply line or to provide other energy sources in the components.

This configuration also makes it possible to supply the field devices with energy, for example.

According to a further preferred embodiment variant, the motor head piece comprises a communication interface which is electrically connected to the communicator electronics, and a feeder interface, to which a feeder cable can be electrically connected, wherein the feeder interface can be electrically connected to evaluation electronics of the evaluation unit, wherein the motor head electronics are connected between the communication interface and the feeder interface, wherein the motor head electronics are configured to communicate signals between the communicator electronics electrically connected to the communication interface and evaluation electronics which can be electrically connected to the feeder interface. The feeder interface is used, in particular, to connect an evaluation unit, in particular its evaluation electronics, to the motor head piece, in particular its motor head electronics, preferably via a feeder cable.

The motor head electronics may preferably be designed to transmit and/or receive signals via the communication interface and/or the feeder interface. In this case, the motor head electronics may be designed, in particular, to convert signals from the communication interface into signals of the feeder interface. Furthermore, the adapter electronics may be designed, in particular, to convert signals from the feeder interface into signals of the communication interface.

It is also preferred if the motor head electronics are configured to transmit signals, which are based on a bus protocol, to the communicator electronics of the communicator pieces via a bus system or a plurality of bus systems or to receive them from the communicator electronics of the communicator pieces. This configuration makes it possible to electrically connect all communication units to the motor head piece via a bus line. As a result, the motor head piece may receive signals from the communication units via this one bus line and/or may transmit signals to the communication units via this one bus line. It is also advantageous that the signals can be transmitted at the same time via the bus line. It is also possible to provide two or more bus lines, in particular, two or more different bus systems.

In one variant, the motor head piece may be configured to be coupled in terms of signaling to the evaluation unit via a bus line.

In one variant, the motor head piece may be able to be coupled in terms of signaling to a drive unit and may be designed to control the drive unit.

The adapter piece and/or the communicator piece and/or the motor head piece may preferably have a storage unit which is designed to store signals.

According to one preferred embodiment, the adapter piece may comprise a polymer, a plastic, a glass fiber reinforced nylon, a glass fiber reinforced acetyl, aluminum, or an aluminum alloy or may be composed of a polymer, a plastic, a glass fiber reinforced nylon, a glass fiber reinforced acetyl, aluminum, or an aluminum alloy.

The communicator piece may preferably comprise a polymer, a plastic, a glass fiber reinforced nylon, a glass fiber reinforced acetyl, aluminum, or an aluminum alloy or may be composed of a polymer, a plastic, a glass fiber reinforced nylon, a glass fiber reinforced acetyl, aluminum, or an aluminum alloy.

The motor head piece may preferably comprise a polymer, a plastic, a glass fiber reinforced nylon, a glass fiber reinforced acetyl, anodized metal, aluminum, or an aluminum alloy or may be composed of a polymer, a plastic, a glass fiber reinforced nylon, a glass fiber reinforced acetyl, anodized metal, aluminum, or an aluminum alloy.

Particularly preferably, the communication units may each comprise a field device, wherein the adapter electronics are electrically connected to the field device electronics of the field device.

For further advantages, embodiment variants and embodiment details of this third aspect and its possible developments, reference is also made to the above description of the corresponding features and developments of the first and second aspects.

According to a further aspect of the invention, the object mentioned at the outset is achieved by the use of a data transmission unit for an end plate and/or for a bioreactor.

According to a further aspect of the invention, the object mentioned at the outset is achieved by means of a method for providing a data transmission unit, having the steps of: providing a motor head piece which can be coupled in terms of signaling to an evaluation unit and can be coupled in terms of energy to a drive unit which can be arranged on an end plate of a bioreactor, comprising motor head electronics, and assembling communication units, comprising the steps of: selecting adapter pieces each having adapter electronics on the basis of the field devices to be coupled to these adapter pieces, providing communicator pieces each having communicator electronics, coupling the adapter pieces to a respective communicator piece of the communicator pieces and respectively electrically connecting the adapter electronics to the communicator electronics, respectively electrically connecting the communicator electronics to the motor head electronics.

As a result of the modular system, the adapter pieces can be selected on the basis of a field device and can be coupled to the latter. This system preferably comprises different groups of adapter pieces which are preferably configured in accordance with different field devices.

The communicator pieces may preferably be substantially identical and may be designed to be coupled to each of the adapter pieces.

In particular, it is therefore possible to provide a data transmission unit which is individually adapted to customer requirements. It is also advantageous that a data processing unit may also be retrofitted and/or upgraded.

For further advantages, embodiment variants, and embodiment details of these further aspects and their possible developments, reference is also made to the above description of the corresponding features and developments of the first, second, and third aspects.

BRIEF DESCRIPTION OF THE DRAWINGS

Preferred exemplary embodiments are explained, by way of example, on the basis of the accompanying figures, in which.

DETAILED DESCRIPTION OF THE EMBODIMENTS

In the Figures, identical or substantially functionally identical or similar elements are denoted using the same reference signs.

Figure 1:
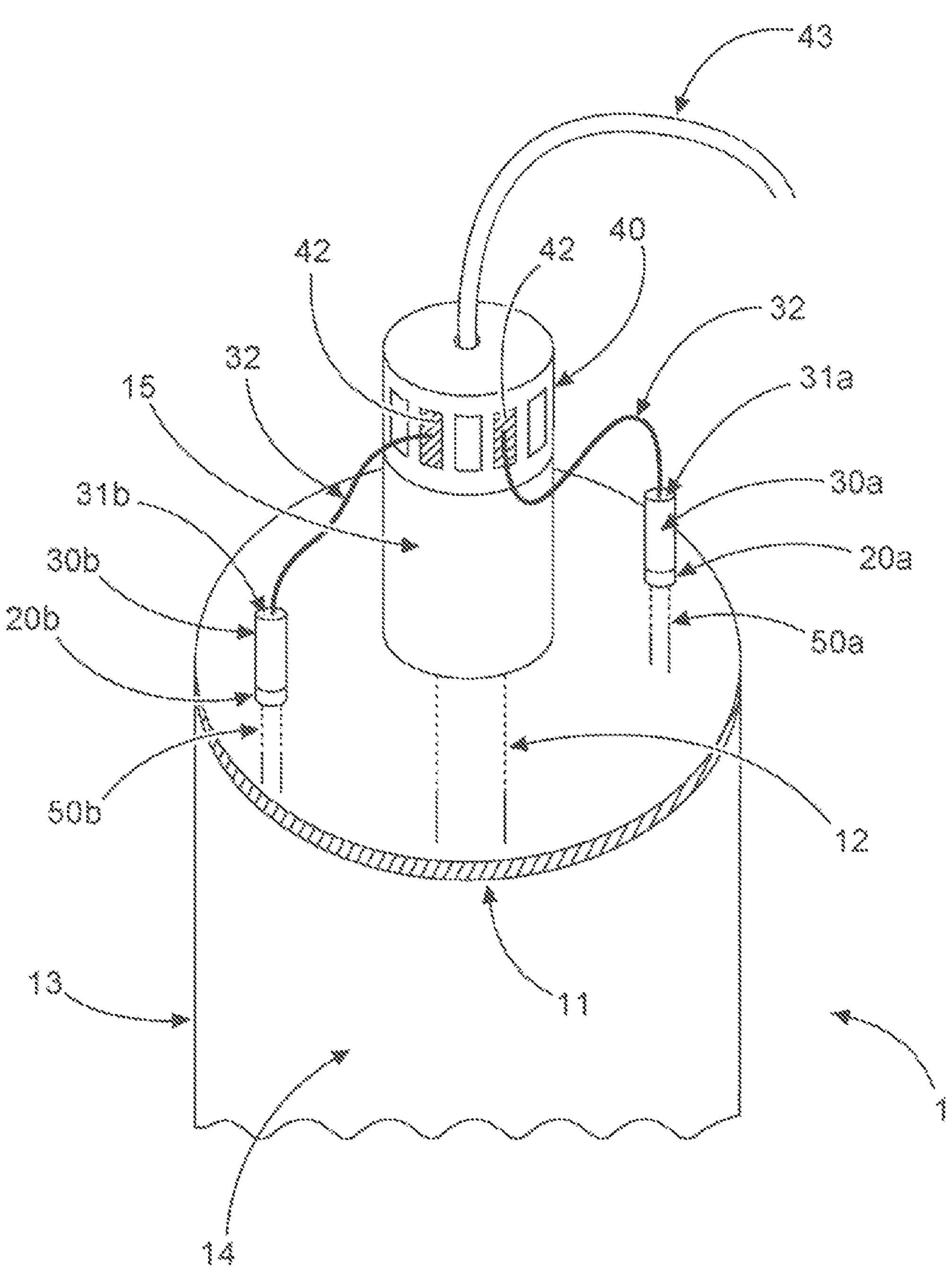
FIG. 1 shows a section of a bioreactor.

FIG. 1 shows a section of a bioreactor 1 having a container 13 and an end plate 11 which closes the container 13. The container 13 or its wall and the end plate 11 surround an interior 14. The interior 14 may define a reaction chamber of the bioreactor 1.

The bioreactor 1 also comprises an agitator shaft 12 which is guided into the interior 14 and is coupled to a drive unit 15 which is arranged on the end plate 11. The drive unit 15 can be used to cause the agitator shaft 12 and therefore an agitator of the bioreactor 1 to rotate in order to thoroughly mix contents, preferably a reaction medium.

The bioreactor 1 shown in FIG. 1 also comprises two field devices 50*a*, 50*b* which are each coupled to a communication unit. The communication units are parts of the data transmission unit.

Configurations having only one field device and only one communication unit or having more than two field devices and accordingly more than two communication units are also possible. Configurations in which two or more field devices are connected to a common communicator piece using a respective adapter piece are also possible.

The data transmission unit comprises a motor head piece 40 which is installed on the drive unit 15 and is coupled at least in terms of energy to the latter. The motor head piece 40 is therefore designed to supply the drive unit 15 with energy. In particular, motor head electronics may be electrically connected to drive electronics of the drive unit 40.

The motor head piece 40 may preferably be designed to be coupled in terms of signaling to the drive unit 15. As a result, the motor head electronics can preferably also control the drive unit.

A feeder cable 43 is connected to the motor head piece 40. This feeder cable 43 may preferably comprise at least four wires, two for supplying energy and two for transmitting data. The motor head piece 40 can be electrically connected to an evaluation unit via the feeder cable 43. The signal-carrying wires may make it possible to transmit data according to the EIA485/RS485 standard, for example. The use of a differential-based transmission technology enables particularly robust communication which is not susceptible to errors.

The motor head electronics may preferably be designed to transmit signals to the evaluation unit using Modbus, for example, or to receive signals from the evaluation unit. The motor head electronics may also be designed to operate, during bridge operation, between the field devices and the evaluation unit or a control unit and additionally as a hub for field devices on a bioreactor.

The evaluation unit may preferably be designed to receive signals, preferably from the data transmission unit, and to evaluate said signals. The evaluation unit may also be designed to generate signals and to transmit them to the data transmission unit. These signals may preferably be used to control and/or calibrate the field devices 50*a*, 50*b*. Particularly preferably, the evaluation unit may receive signals from the data transmission unit, may evaluate these signals and, on the basis of these signals, may generate signals and transmit them to the data transmission unit.

The communication units each comprise an adapter piece 20*a*, 20*b* and a communicator piece 30*a*, 30*b*. The adapter piece 20*a*, 20*b* comprises adapter electronics which are electrically connected to the field device electronics of one of the field devices 50*a*, 50*b*. The communicator piece 30*a*, 30*b* comprises communicator electronics which are electrically connected to the adapter electronics and to the motor head electronics of the motor head 40.

The motor head piece 40 shown in FIG. 1 is connected to the communicator pieces 30*a*, 30*b* in a wired manner. For this purpose, the motor head piece 40 has sockets 42 which are each in the form of a communication interface. The motor head interfaces 31*a*, 31*b* of the communicator piece 30*a*, 30*b* are each in the form of a connection on a cable 32, wherein the cable 32 can be permanently or releasably fitted to the motor head interfaces 31*a*, 31*b*. In this case, the connection is in the form of a connector which is configured to be connected to contacts of the socket 42 on the motor head piece 40.

This configuration makes it possible to communicate signals between the field devices 50*a*, 50*b* and the adapter pieces 20*a*, 20*b* and between the adapter pieces 20*a*, 20*b* and the communicator pieces 30*a*, 30*b* and between the communicator pieces 30*a*, 30*b* and the motor head piece 40. The adapter electronics not shown in FIG. 1 each comprise a signal converter in order to convert the signals from the field device 50*a*, 50*b*, preferably into standardized signals, and to transmit the signals to communicator electronics of the communicator piece 30*a*, 30*b*. The adapter electronics may preferably be designed to receive signals from the communicator electronics, to convert them by means of the signal converter and to transmit them to field device electronics.

The field devices 50*a*, 50*b*, the adapter pieces 20*a*, 20*b*, the communicator pieces 30*a*, 30*b* and the motor head piece 40 are separate components which are coupled to one another.

Signals can be transmitted between at least two field devices 50*a*, 50*b* and the evaluation unit by means of the data transmission unit as a result of the motor head piece 40 being coupled in terms of signaling to the evaluation unit and the respective adapter piece 20*a*, 20*b* being coupled in terms of signaling to the field device 50*a*, 50*b*.

Different field devices 50*a*, 50*b* are generally configured to transmit different signals carrying field device information and measurement information and/or to receive different signals carrying control information. For example, field devices 50*a*, 50*b* may transmit and/or receive digital or analog signals. In particular, field devices 50*a*, 50*b* may generate analog signals. For this reason, it is necessary to use accordingly configured adapter pieces 20*a*, 20*b* in order to be able to convert these signals and to be able to transmit them to the communicator piece 30*a*, 30*b* and/or in order to be able to receive these signals from the communicator piece 30*a*, 30*b*, to convert them and to transmit them to the field device 50*a*, 50*b*.

In contrast to the adapter piece 20*a*, 20*b*, the communicator piece 30*a*, 30*b* may preferably have an identical design for each communication unit. The communicator pieces 30*a*, 30*b* may therefore preferably have a standard configuration. Communicator electronics of each communicator piece 30*a*, 30*b* are electrically connected to the motor head electronics in order to receive signals from the field device 50*a*, 50*b* via the adapter piece 20*a*, 20*b* and to transmit these signals to the motor head electronics and/or to receive signals from the motor head electronics and to transmit them to the field device 50*a*, 50*b* via the adapter piece 20*a*, 20*b*. As a result, the motor head electronics can receive signals from the individual field devices 50*a*, 50*b* and/or can transmit signals to the latter.

As a result of different adapter pieces 20*a*, 20*b* which are configured in accordance with the field devices 50*a*, 50*b*, the bioreactor 1, in particular, the data transmission unit, can be individually adapted to customer requirements. As a result, only an accordingly configured adapter piece 20*a*, 20*b* must be designed on the hardware side—the outlay involved in integrating a new field device 50*a*, 50*b* in the bioreactor 1 is therefore considerably lower.

Figure 2:
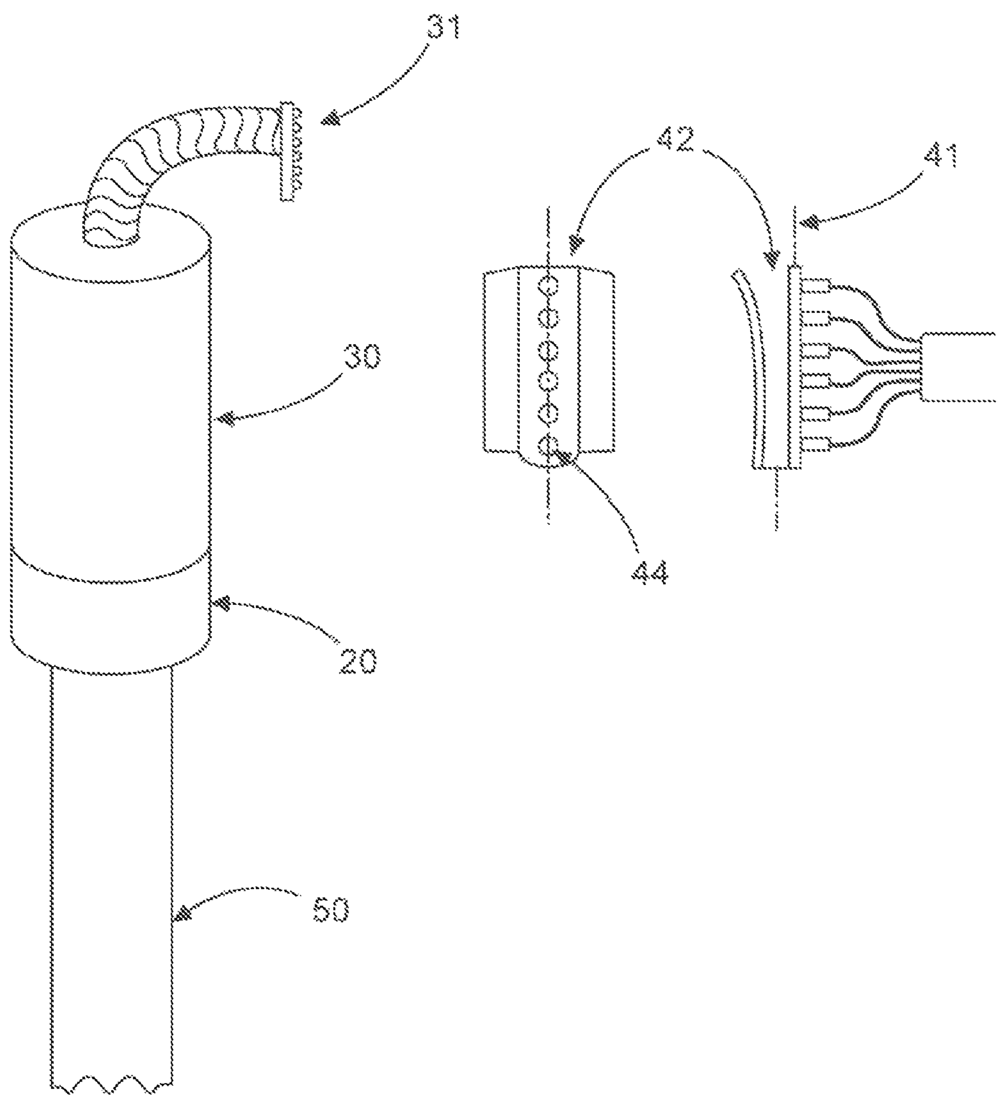
FIG. 2 shows a data transmission unit having a communication unit.

FIG. 2 shows, on the left, a communication unit which is coupled to a field device 50 and has an adapter piece 20 and a communicator piece 30. According to the exemplary embodiment shown here, the adapter piece 20 is installed directly on the field device 50 and is electrically connected to the latter. The communicator piece 30 is likewise installed directly on the adapter piece 20 and is connected to the latter. The communicator piece 30 has a motor head interface 31 which is in the form of a connection on a cable. In this case, the connection is in the form of a connector which is configured to be connected to contacts 44 of a socket 42 on the motor head piece. The socket 42 is formed on a housing 41 of the motor head piece.

Figure 3:
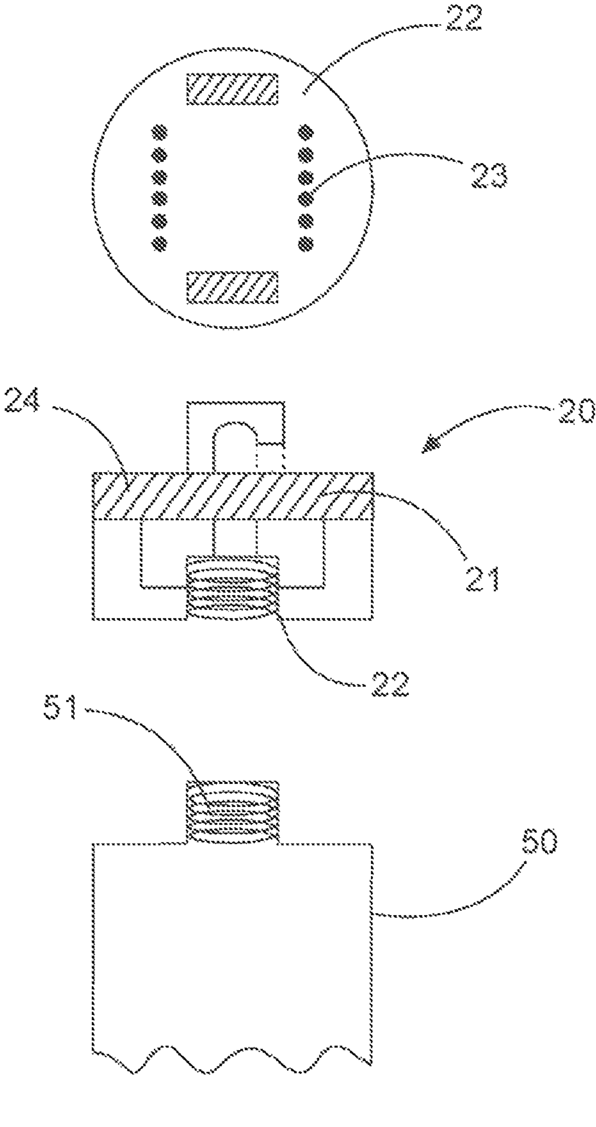
FIG. 3 shows an adapter piece which can be coupled to a field device and a section of a field device.

FIG. 3 shows a field device 50 having a connection interface 51 which can be coupled to a field device interface 22 of the adapter piece 20. The connection interface 51 and the field device interface 22 make it possible to couple the field device 50 to the adapter piece 20. The adapter electronics not illustrated in FIG. 3 are accommodated on a printed circuit board, a PCBA, 24.

The adapter piece 20 has a field device interface 22 which is in the form of pins 23 on the printed circuit board 24. According to the example shown here, the printed circuit board 24 has a total of six pairs of pins 23. At least two pins thereof may be configured, for example, to enable an electrical connection between the adapter electronics and the field device electronics, wherein these pins 23 are preferably configured as outputs and/or inputs. In addition, the printed circuit board 24 may preferably have two pins 23 which are configured to supply energy. The printed circuit board 24 may have, in particular, two spring contacts which enable an electrical connection between the adapter electronics and the communicator electronics. The printed circuit board 24 could have, for example, the following sample assignment: +24 V, GND, RS485+, RS485−, Analog1, Analog2.

The pins 23 may preferably have partial metallization of the contact areas, in particular, gold plating.

Figure 4:
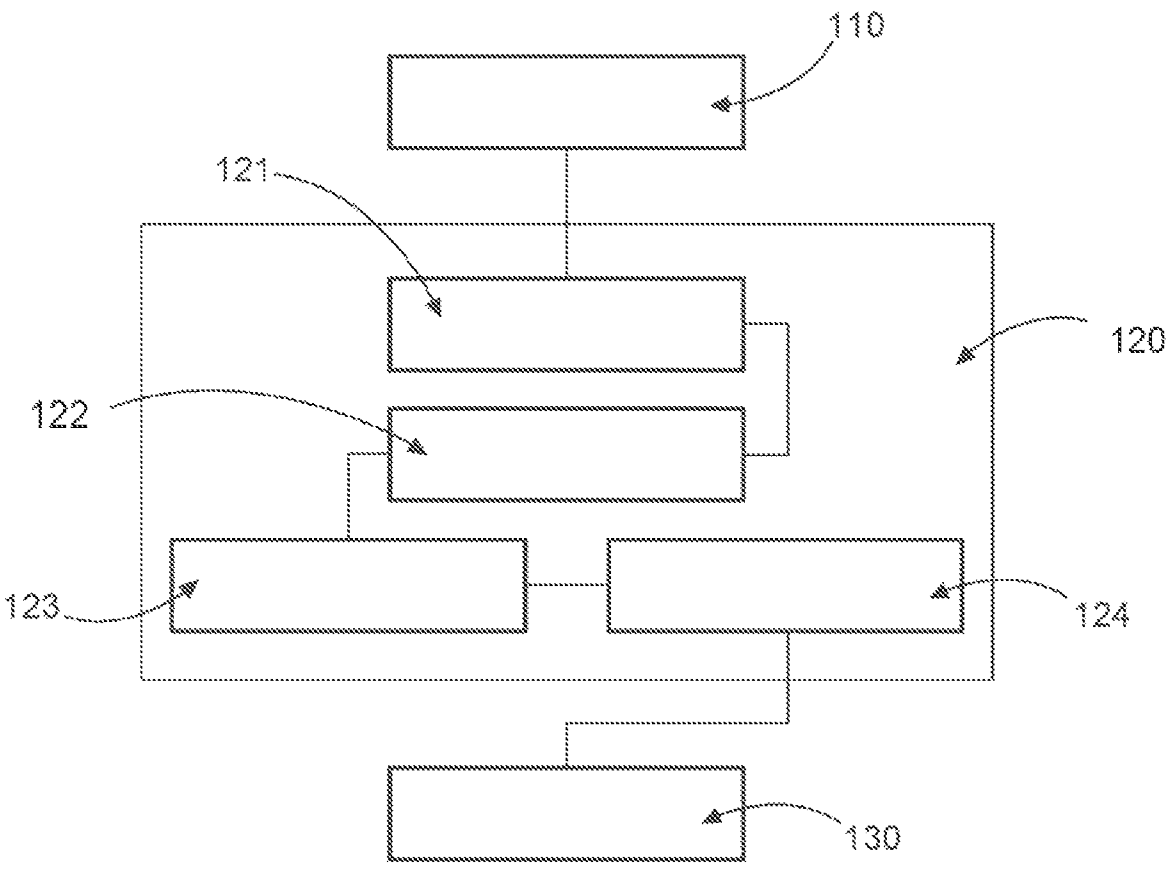
FIG. 4 shows exemplary method steps for providing a data transmission unit.

FIG. 4 shows exemplary method steps for providing a data transmission unit. In this case, a motor head piece which can be coupled in terms of signaling to an evaluation unit and can be coupled in terms of energy to a drive unit which can be arranged on an end plate of a bioreactor, comprising motor head electronics, is selected or provided in a step 110. In a further step 120, communication units are assembled. Step 120 of assembling the communication units also comprises a step 121 of selecting adapter pieces each having adapter electronics on the basis of the field devices to be coupled to these adapter pieces, and a step 122 of providing communicator pieces each having communicator electronics, and a step 123 of coupling the adapter pieces to a respective communicator piece of the communicator pieces, and a respective step 124 of electrically connecting the adapter electronics to the communicator electronics. The communicator electronics are also electrically connected to the motor head electronics in a step 130.

The invention claimed is:

1. A bioreactor for culturing microorganisms and/or cell cultures, comprising:
- a container;
- an end plate adapted to close the container;
- an agitator further comprising:
  - an agitator shaft guided through the end plate into an interior of the container; and
  - an agitator element connected to the agitator shaft in the interior of the container;
- a drive unit disposed on the end plate and coupled to the agitator shaft; and
- at least one field device disposed in the interior and which further comprises field device electronics, wherein the end plate comprises:
  - an inner side and an outer side opposite the inner side;
  - an agitator connection device adapted to:
    - guide the agitator shaft through the end plate; and
    - connect the drive unit;
  - at least one field device connection device adapted to connect the field device on the inner side; and
  - a data transmission unit disposed on the outer side and which further comprises:
    - a motor head piece communicatively coupled to an evaluation unit and electrically coupled to the drive unit, comprising motor head electronics; and
    - at least one communication unit communicatively coupled to the motor head piece, the at least one communication unit comprising:
      - an adapter piece having adapter electronics which are electrically connected to the field device electronics of the field device; and
      - a communicator piece having communicator electronics which are electrically connected to the adapter electronics and to the motor head electronics;
      - wherein the adapter electronics are configured to communicate signals between the field device electronics and the communicator electronics, wherein the signals carry field device information and measurement information and/or control information;

wherein the communicator electronics are configured to communicate the signals between the adapter electronics and the motor head electronics; and wherein the data transmission unit also comprises a signal converter which is part of the adapter electronics and/or part of the communicator electronics;

wherein the adapter piece and the communicator piece are in the form of separate components coupled to one another; and wherein the motor head piece is in the form of a separate component coupled to the communication unit.

2. An end plate for closing a bioreactor, comprising:

an inner side and an outer side opposite the inner side;

an agitator connection device adapted to:

guide an agitator shaft through the end plate; and connect a drive unit to the agitator shaft; and at least one field device connection device adapted to connect a field device on the inner side;

a data transmission unit disposed on the outer side and having:

a motor head piece communicatively coupled to an evaluation unit and electrically coupled to the drive unit disposed on the outer side, the motor head piece comprising motor head electronics; and at least one communication unit communicatively coupled to the motor head piece, comprising:

an adapter piece having adapter electronics be electrically connected to field device electronics of the field device; and a communicator piece having communicator electronics which are electrically connected to the adapter electronics and to the motor head electronics;

wherein the adapter electronics are adapted to communicate signals between the field device electronics and the communicator electronics, wherein the signals carry field device information and measurement information and/or control information;

wherein the communicator electronics are adapted to communicate the signals between the adapter electronics and the motor head electronics;

wherein the data transmission unit also comprises a signal converter which is part of the adapter electronics and/or part of the communicator electronics, wherein the adapter piece and the communicator piece are in the form of separate components coupled to one another; and wherein the motor head piece is in the form of a separate component coupled to the communication unit.

3. A data transmission unit for an end plate of a bioreactor, having:

a motor head piece communicatively coupled to an evaluation unit and electrically coupled to a drive unit disposed on an end plate of a bioreactor, the motor head piece comprising motor head electronics; and at least one communication unit communicatively coupled to the motor head piece, respectively comprising:

an adapter piece having adapter electronics electrically connected to a field device electronics of a field device; and a communicator piece having communicator electronics which are electrically connected to the adapter electronics and to the motor head electronics;

wherein the adapter electronics are adapted to communicate signals between the field device electronics and the communicator electronics, wherein the signals carry field device information and measurement information and/or control information;

wherein the communicator electronics are adapted to communicate the signals between the adapter electronics and the motor head electronics;

wherein the data transmission unit also comprises a signal converter which is part of the adapter electronics and/or part of the communicator electronics;

wherein the adapter piece and the communicator piece are in the form of separate components coupled to one another; and wherein the motor head piece is in the form of a separate component coupled to the at least one communication unit.

4. The data transmission unit as claimed in at least claim 3, wherein:

the adapter piece comprises a field device interface and a communicator interface, wherein the adapter electronics:

are connected between the field device interface and the communicator interface, and are electrically connected to the field device electronics via the field device interface; and are electrically connected to the communicator electronics via the communicator interface; and the communicator piece comprises an adapter interface and a motor head interface, wherein the communicator electronics:

are connected between the adapter interface and the motor head interface;

are electrically connected to the adapter electronics via the adapter interface; and are electrically connected to the motor head electronics via the motor head interface.

5. The data transmission unit as claimed in claim 3 comprising at least one first group of first adapter pieces and one second group of second adapter pieces:

wherein the adapter electronics of the first adapter pieces are adapted to communicate the signals between the field device electronics of a first field device and the communicator electronics;

wherein the adapter electronics of the second adapter pieces are adapted to communicate the signals between the field device electronics of a second field device and the communicator electronics; and wherein the adapter piece of each communication unit is selected from at least the first group of first adapter pieces and the second group of second adapter pieces on the basis of a field device to be coupled.

6. The data transmission unit as claimed in claim 3, wherein the adapter piece comprises a field device coupling adapted to connect the field device to the adapter piece mechanically.

7. The data transmission unit of claim 6, wherein the field device is releasably coupled to the adapter piece.

8. The data transmission unit as claimed in claim 3, wherein the communicator piece comprises an adapter coupling adapted to connect the adapter piece to the communicator piece mechanically.

9. The data transmission unit as claimed in claim 8, wherein the communicator piece is releasably coupled to the adapter piece.

10. The data transmission unit as claimed in claim 3:

wherein the signal converter is an analog/digital converter; or wherein the adapter electronics, the communicator electronics, or the signal converter is adapted to receive analog signals to convert them into standardized analog signals, to convert the standardized analog signals into digital signals, to transmit the digital signals, or vice versa.

11. The data transmission unit as claimed in claim 3, wherein the communicator electronics or the motor head electronics are adapted to receive the signals without or with contact, to convert the signals into radio signals, to transmit them by radio or in a wired manner, or vice versa.

12. The data transmission unit as claimed in claim 3, wherein the adapter electronics are adapted to receive the signals without or with contact, to convert the signals into radio signals, to transmit them by radio or in a wired manner, or vice versa.

13. The data transmission unit as claimed in claim 4, wherein the field device interface, the communicator interface, the adapter interface, or the motor head interface are in the form of a connection on a cable.

14. The data transmission unit as claimed in claim 13, wherein the cable has a length of at most 50 cm.

15. The data transmission unit as claimed in claim 3, wherein:

the motor head piece is electrically coupled to the communicator piece, wherein the motor head electronics are adapted to supply the communicator electronics with power;

the communicator piece is electrically coupled to the adapter piece, wherein the communicator electronics are adapted to supply the adapter electronics with power; and/or the adapter piece is electrically coupled to the field device, wherein the adapter electronics are adapted to supply the field device electronics with power;

wherein the power is transmitted with contact in a wired manner or inductively.

16. The data transmission unit as claimed in claim 3, wherein the motor head piece comprises:

a communication interface electrically connected to the communicator electronics; and a feeder interface, to which a feeder cable is electrically connected, wherein the feeder interface is electrically connected to evaluation electronics of the evaluation unit, wherein the motor head electronics are connected between the communication interface and the feeder interface, wherein the motor head electronics are adapted to communicate signals between the communicator electronics electrically connected to the communication interface and evaluation electronics electrically connected to the feeder interface.

17. The data transmission unit as claimed in claim 3, wherein the motor head electronics are adapted to transmit signals, which are based on a bus protocol, to the communicator electronics of the communicator piece via a bus system or a plurality of bus systems or to receive them from the communicator electronics of the communicator piece.

18. An end plate incorporating the data transmission unit as claimed in claim 3, the end plate comprising:

an inner side and an outer side opposite the inner side;

an agitator connection device adapted to:

guide an agitator shaft through the end plate; and connect a drive unit coupled to the agitator shaft; and at least one field device connector adapted to connect the field device on the inner side, wherein the data transmission unit is disposed on the outer side.

19. A bioreactor incorporating the data transmission unit as claimed in claim 3, the bioreactor comprising:

a container;

an end plate adapted to close the container;

an agitator comprising:

an agitator shaft guided through the end plate into an interior of the container; and an agitator element connected to the agitator shaft in the interior of the container;

a drive unit disposed on the end plate and coupled to the agitator shaft; and at least one field device disposed in the interior, the at least one field device comprising field device electronics, wherein the end plate comprises:

an inner side and an outer side opposite the inner side;

an agitator connection device adapted to:

guide the agitator shaft through the end plate; and connect the drive unit;

at least one field device connector adapted to connect the field device on the inner side; and the data transmission unit disposed on the outer side.

20. A method for providing a data transmission unit, having the steps of:

providing a motor head piece communicatively coupled to an evaluation unit and electrically coupled to a drive unit disposed on an end plate of a bioreactor, the motor head piece comprising motor head electronics; and assembling at least one communication unit, comprising the steps of:

selecting an adapter piece having adapter electronics on the basis of a field device to be coupled to this adapter piece;

providing a communicator piece having communicator electronics;

coupling the adapter piece to the communicator piece and electrically connecting the adapter electronics to the communicator electronics; and electrically connecting the communicator electronics to the motor head electronics.

* * * * *